United States Patent
March et al.

(10) Patent No.: US 9,333,110 B2
(45) Date of Patent: *May 10, 2016

(54) VALVE FOR OSTOMY POUCH

(71) Applicant: Hollister Incorporated, Libertyville, IL (US)

(72) Inventors: Daniel March, Lake Villa, IL (US); John F. Hannan, Enniscrone (IE); Terence King, Antioch, IL (US); Jakub Goczkowski, København NV (DK)

(73) Assignee: Hollister Incorporated, Libertyville, IL (US)

( * ) Notice: Subject to any disclaimer, the term of this patent is extended or adjusted under 35 U.S.C. 154(b) by 10 days.

This patent is subject to a terminal disclaimer.

(21) Appl. No.: 14/487,713

(22) Filed: Sep. 16, 2014

(65) Prior Publication Data

US 2015/0025483 A1   Jan. 22, 2015

Related U.S. Application Data

(63) Continuation of application No. 13/301,395, filed on Nov. 21, 2011, now Pat. No. 8,882,732.

(60) Provisional application No. 61/416,072, filed on Nov. 22, 2010.

(51) Int. Cl.
*A61M 1/06* (2006.01)
*A61F 5/44* (2006.01)
*A61F 5/445* (2006.01)
*F16K 3/24* (2006.01)

(52) U.S. Cl.
CPC .............. *A61F 5/4405* (2013.01); *A61F 5/445* (2013.01); *F16K 3/24* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 3,481,336 A | * | 12/1969 | Ipson | ...................... | A61F 5/445 604/342 |
| 4,055,179 A | * | 10/1977 | Manschot | ............. | A61F 5/4405 251/333 |
| 4,147,184 A | * | 4/1979 | Jess | ....................... | F16K 5/0292 137/625.47 |
| 4,238,059 A | * | 12/1980 | Caraway | ................ | A61F 5/445 222/529 |
| 4,280,498 A | * | 7/1981 | Jensen | .................. | A61F 5/4405 251/310 |
| 4,300,560 A | * | 11/1981 | Steer | ...................... | A61F 5/445 222/530 |
| 4,443,219 A | * | 4/1984 | Meisch | ................. | A61F 5/4405 604/256 |
| 4,592,750 A | * | 6/1986 | Kay | ....................... | A61F 5/4404 604/277 |

(Continued)

FOREIGN PATENT DOCUMENTS

GB    2202032 A    9/1988

*Primary Examiner* — Tatyana Zalukaeva
*Assistant Examiner* — Guy K Townsend
(74) *Attorney, Agent, or Firm* — Levenfeld Pearlstein, LLC (57) ABSTRACT

A valve that is sealable to an associated container having an interior fluid storage region is adapted to permit and stop flow of fluid from the fluid storage region. The valve includes a valve body sealable to the container and a stem mounted to the valve body having a portion in flow communication with the fluid storage region. The stem is movable relative to the valve body between an open position to permit flow from the fluid storage region through the valve, and a closed position to stop flow through the valve. The stem has a grasping region spaced from the valve body. The grasping region is adapted rotate the stem to move the valve between the open and closed positions. The grasping region has first and second sides. One of the sides has a tactile indicator to provide indication of the position of the valve, the other of the side is devoid of the tactile indicator.

20 Claims, 13 Drawing Sheets

(56) References Cited

U.S. PATENT DOCUMENTS

| | | | | |
|---|---|---|---|---|
| 4,668,227 A * | 5/1987 | Kay | | A61F 5/442 134/57 R |
| D295,220 S * | 4/1988 | Kay | | D24/121 |
| 4,790,833 A * | 12/1988 | Schmidt | | A61M 1/0019 604/317 |
| 4,844,415 A * | 7/1989 | Nielsen | | F16K 5/0442 251/100 |
| D303,574 S * | 9/1989 | Steer | | D24/118 |
| D303,575 S * | 9/1989 | Steer | | D24/118 |
| 4,909,478 A * | 3/1990 | Steer | | A61F 5/4407 251/352 |
| 5,226,564 A * | 7/1993 | Steer | | A61F 5/4404 222/107 |
| 5,299,777 A * | 4/1994 | Milstead | | F01M 11/0408 184/1.5 |
| 5,401,264 A * | 3/1995 | Leise, Jr. | | A61F 5/441 604/333 |
| 5,443,453 A * | 8/1995 | Walker | | F16K 11/0853 137/625.41 |
| 5,683,372 A * | 11/1997 | Colacello | | A61F 5/441 604/277 |
| 5,771,590 A * | 6/1998 | Colacello | | A61F 5/441 30/360 |
| D396,731 S * | 8/1998 | Mirto | | D24/118 |
| 5,902,294 A * | 5/1999 | Edwards | | F16K 5/0414 251/287 |
| 5,951,532 A * | 9/1999 | Olsen | | A61F 5/445 604/332 |
| 5,968,024 A * | 10/1999 | Freeman | | A61F 5/4407 604/323 |
| 6,132,407 A * | 10/2000 | Genese | | A61F 5/4405 222/559 |
| 6,485,476 B1 * | 11/2002 | von Dyck | | A61F 5/441 600/29 |
| 6,659,988 B1 * | 12/2003 | Steer | | A61F 5/441 604/333 |
| 7,008,407 B1 * | 3/2006 | Kamp | | A61F 5/4405 604/327 |
| D671,620 S * | 11/2012 | March | | D23/233 |
| 2002/0077611 A1 * | 6/2002 | von Dyck | | A61F 5/442 604/333 |
| 2007/0287953 A1 * | 12/2007 | Ziv | | A61M 39/223 604/31 |
| 2009/0082743 A1 * | 3/2009 | Buglino | | A61F 5/4405 604/335 |
| 2009/0163883 A1 * | 6/2009 | Christensen | | A61F 5/4405 604/328 |
| 2012/0130329 A1 * | 5/2012 | March | | A61F 5/4405 604/332 |
| 2012/0259300 A1 * | 10/2012 | Bjerregaard | | A61F 5/4405 604/327 |

* cited by examiner

VALVE FOR OSTOMY POUCH

CROSS-REFERENCE TO RELATED APPLICATION

This application is a continuation of U.S. application Ser. No. 13/301,395, filed Nov. 21, 2011, which claims the benefit of Provisional U.S. patent application No. 61/416,072, filed Nov. 22, 2010, the disclosures of which are incorporated herein by reference.

BACKGROUND

The present disclosure is directed to a valve for an ostomy pouch. More particularly, the present disclosure pertains to a valve, for draining liquid waste or bodily fluids such as, for example, from a urostomy pouch, the valve having one or more features providing visual and tactile indication of the state of the valve.

A urostomy appliance or pouch is a medical device that provides a means for the collection of liquid waste formed via an opening into the urinary system, that is diverted externally of the body through a stoma.

The waste collected in the pouch is retained in the pouch, for example, during the daytime, so that the user can discharge or empty the pouch at a convenient time and location. The waste can also be routed through the pouch, for example, during the evening, directly to a remote collection container.

To effect the retention or routing function, a valve is disposed at the bottom or discharge end of the pouch. A typical valve is a plastic ball-cock or pet-cock type-valve that includes a fixed body and a rotating cylindrical valve stem. An opening in the body provides fluid communication from the pouch into a circumferentially disposed section of the body on a side of the stem. The stem includes an opening that extends circumferentially about a portion of the stem that is open to a central opening in the stem. In this manner the stem is rotated 180 degrees between an open position, in which the body opening and stem opening are aligned and a closed position, in which the body opening and the stem opening are not in alignment.

The stem extends through and below the body and includes a flange that extends radially outwardly from the stem. The flange provides a finger rest to allow a user to rotate the stem between the open and closed positions. One known valve includes printed indicia (a printed drop) on the flange to provide visual indicate of the position of the valve. For example, when the indicia is visible (away from the user's body), the valve may be in the open position, and when the indicia is not visible or is facing the user's body, the valve may be in the closed position.

In such a urostomy pouch, the valve is located at the bottom of the pouch, and the pouch is typically secured to the users abdomen above or at about the waistline area. As such, even with printed indicia, because of the valve being below the waistline, it may be difficult to determine whether the valve is open or closed. This can be even more difficult for users that are significantly overweight or obese, and more so in low light conditions where the indicia is too difficult to see.

Accordingly, there is a need for a valve for a urostomy pouch that provide positive indication of the state or position of the valve. Desirably, such a valve provides both visual and tactile indication of the valve position.

BRIEF SUMMARY

A valve is sealable to an associated container, such as an ostomy pouch. An exemplary pouch has an interior, and the valve is adapted to permit and stop flow of fluid from the pouch.

The valve includes a valve body sealable to the container. The valve body has a stem receiver formed therein. The valve body includes a fluid receiving region in communication with the pouch interior.

A stem is mounted to the valve body and has a hollow central portion and a sealed upper portion. The stem is positioned in the stem receiving region and is adapted for rotation within the stem receiving region. The stem includes a stem opening in a portion of a wall thereof. The stem is rotatable between an open position to align the stem opening with the valve body fluid receiving region to permit flow from the pouch through the valve, and a closed position to misalign the stem opening with the valve body fluid receiving region to stop flow through the valve.

The stem has a grasping region spaced from the valve body. The grasping region is adapted to rotate the stem within the stem receiving region to move the valve between the open and closed positions. The grasping region includes a tactile indicator to provide indication of the valve position. Such a valve provides both visual and tactile positive indication of the state or position of the valve. The grasping region can be formed with drainage openings therein.

These and other features and advantages of the present disclosure will be apparent from the following detailed description, in conjunction with the appended claims.

BRIEF DESCRIPTION OF THE SEVERAL VIEWS OF THE DRAWINGS

The benefits and advantages of the present disclosure will become more readily apparent to those of ordinary skill in the relevant art after reviewing the following detailed description and accompanying drawings, wherein.

DETAILED DESCRIPTION

While the present disclosure is susceptible of embodiment in various forms, there is shown in the drawings and will hereinafter be described a presently preferred embodiment with the understanding that the present disclosure is to be considered an exemplification of the disclosure and is not intended to limit the disclosure to the specific embodiment illustrated.

It should be further understood that the title of this section of this specification, namely, "Detailed Description", relates to a requirement of the United States Patent Office, and does not imply, nor should be inferred to limit the subject matter disclosed herein.

Figure 3:
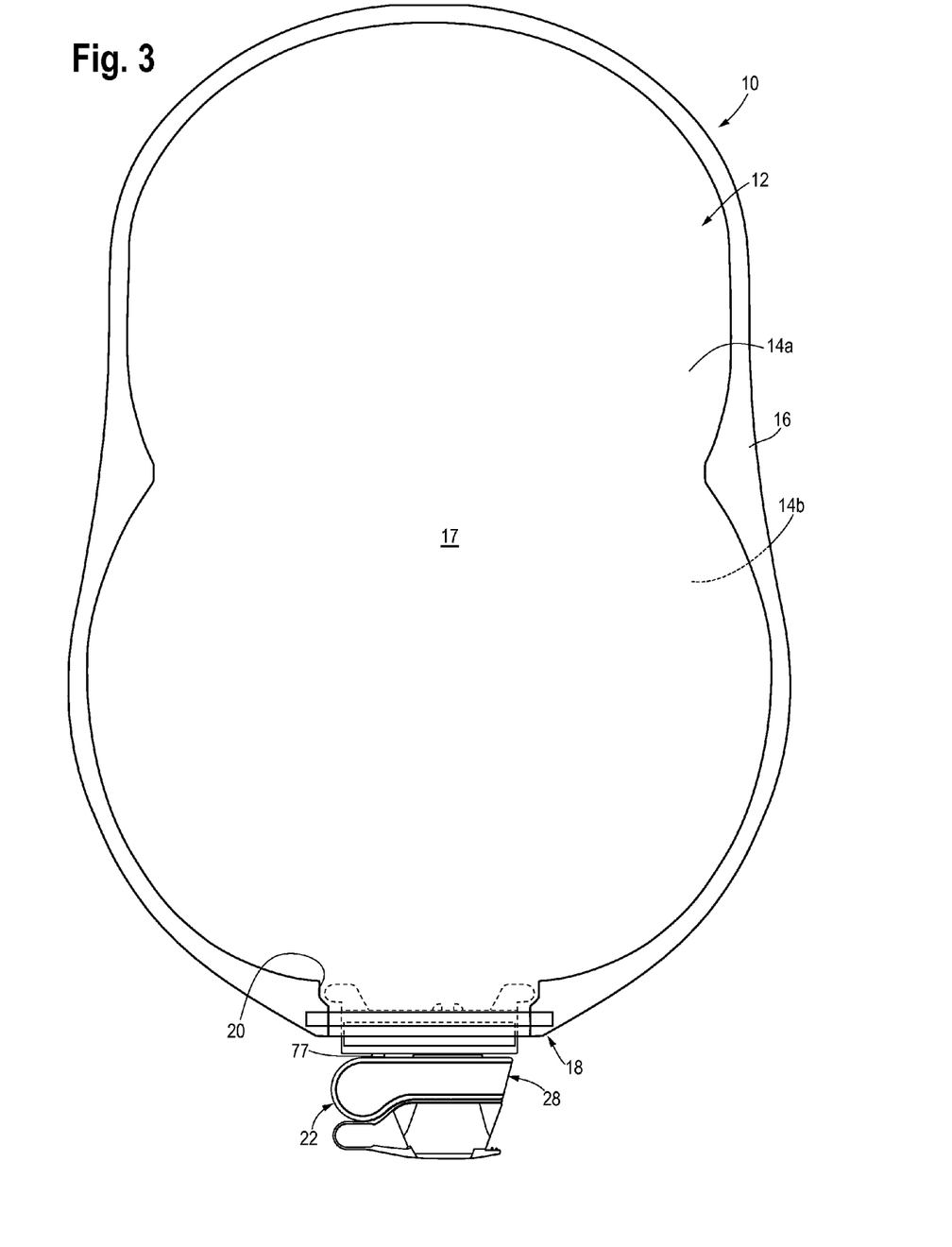
FIG. 3 is a front view of an exemplary pouch having the ostomy valve mounted thereto.

Referring now to the figures and briefly first to FIG. 3, there is shown a urostomy pouch 10 having a body 12 formed by, for example, sealing two films 14a,b to one another about their respective peripheries 16 to define an interior storage region 17. The bottom 18 of the pouch 10 includes an opening 20 into which a valve 22 is fitted and secured. The films 14a,b can be sealed to one another by methods such a heat sealing and the like; the valve 22 being similarly sealed to the pouch 10 at the bottom opening 20. Suitable methods for sealing the pouch walls/films 14 to one another and valve 22 to the pouch films 14 will be recognized by those skilled in the art.

For purposes of the present disclosure and discussion, reference to "bottom," is intended to refer to the lower portion of the pouch 10 and/or valve 22 when the pouch 10 is adhered to a user's body.

Figure 4:
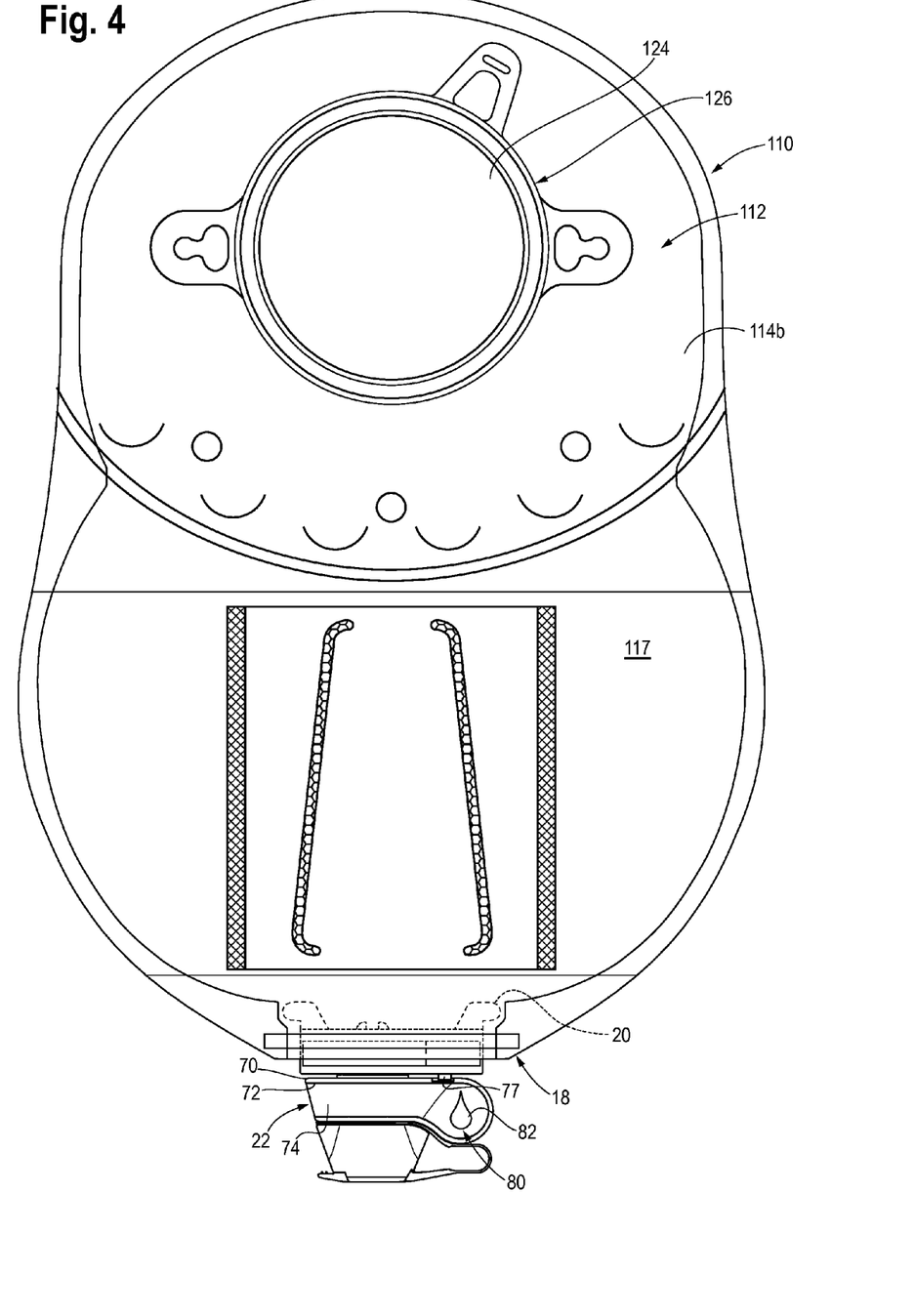
FIG. 4 is a rear view of another exemplary pouch having the ostomy valve mounted thereto.
Figure 5:
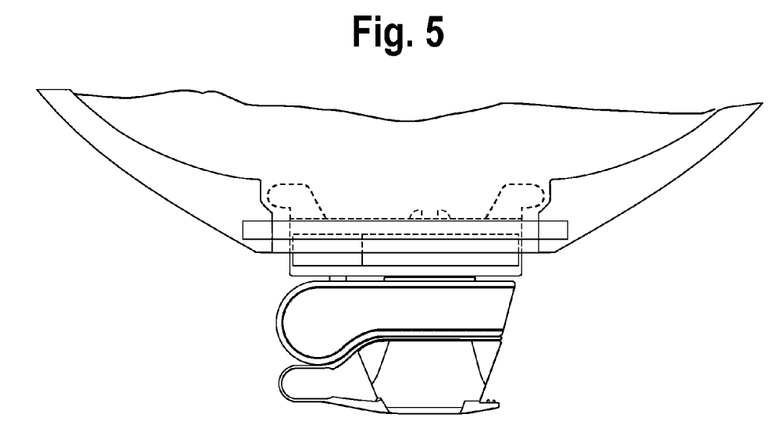
FIG. 5 is an enlarged rear view of the pouch and valve illustrated in FIG. 3.

As seen in FIG. 4, which shows an alternate pouch 110, the pouch 110 also includes an input opening 124 through which waste is input to the pouch 110 from a stoma. The input opening 124 is adhered to the user by a barrier (not shown) in a one-piece or two-piece configuration (the two-piece configuration being shown generally at 126, in FIG. 4), which configurations will also be recognized by those skilled in the art.

The valve 22 is attached and sealed to the pouch bottom 18. Accordingly, the valve 22 includes a body 28 that is sealed to the pouch films 14a,b and a stem portion 30 that is supported in and by the body 28. The stem portion 30 is movable, e.g., rotatable, to open and close the valve 22 (e.g., to permit and isolate flow from the pouch 10).

Figures 1, 1A:
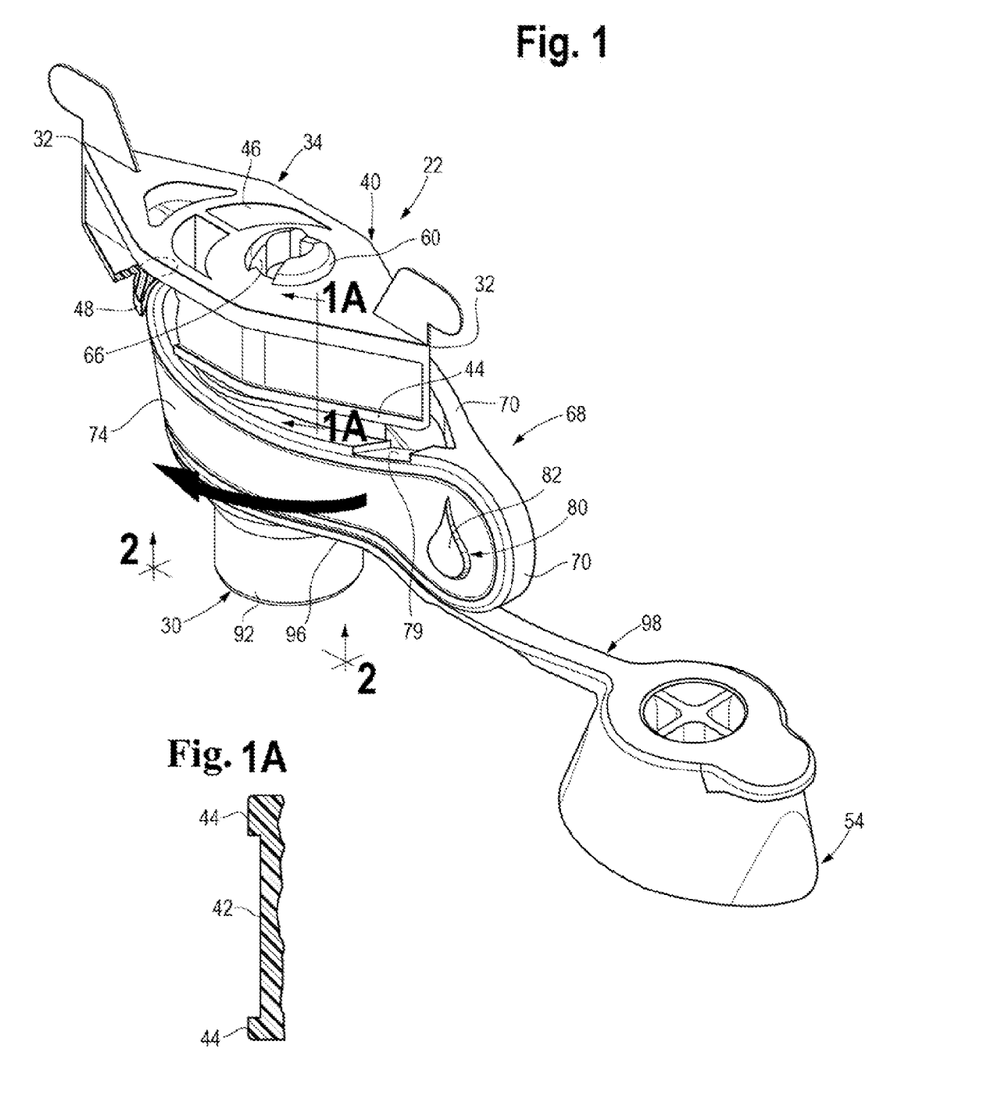
FIG 1 is a perspective view of a valve for an ostomy pouch having tactile indication of valve position and an associated cap tethered to the valve.
FIG. 1A is a sectional view taken along line 1A-1A of FIG. 1.
Figure 10:
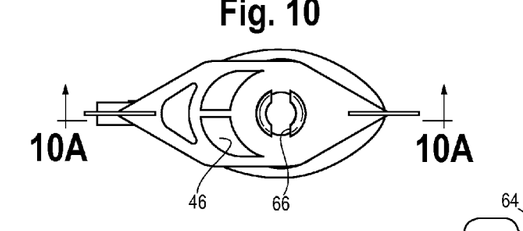
FIG. 10 is a top view of the valve.
Figure 10A:
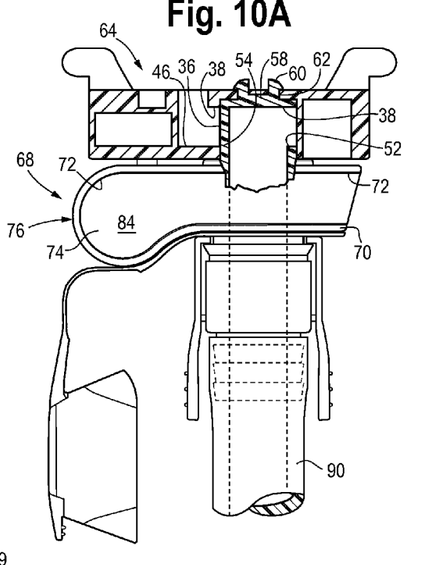
FIG. 10A is a cross-sectional illustration taken along line 10A-10A of FIG. 10, the valve shown in the closed position.
Figure 10B:
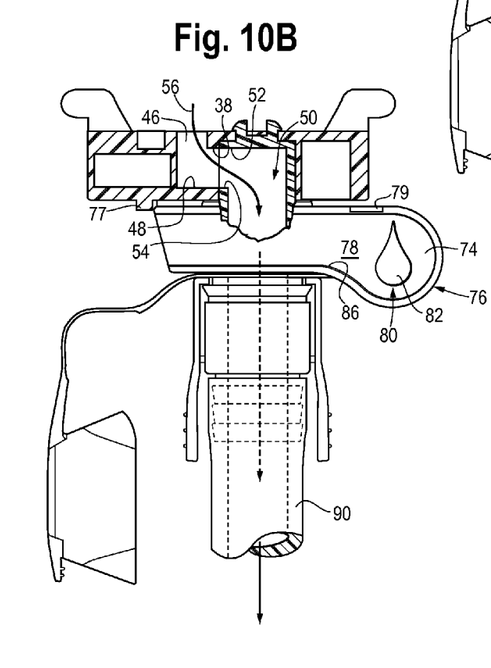
FIG. 10B is a cross-sectional illustration similar to FIG. 10A with the valve shown in the open position.
Figure 11:
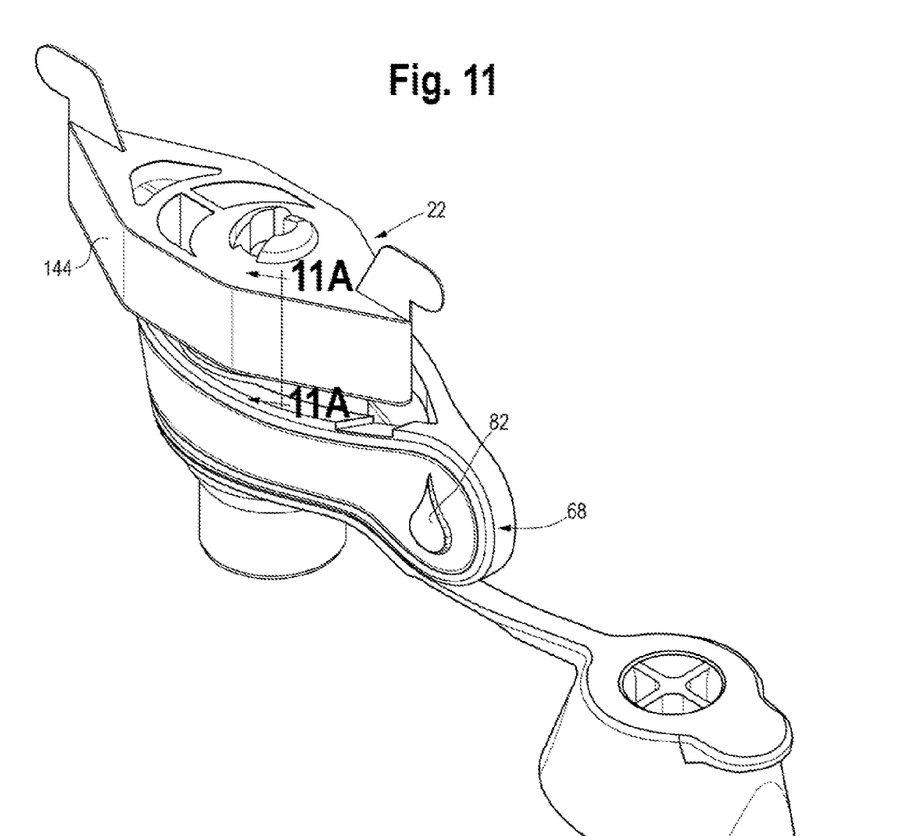
FIG. 11 is a perspective view of an alternate embodiment of a valve for an ostomy pouch having tactile indication of valve position.
Figure 11A:
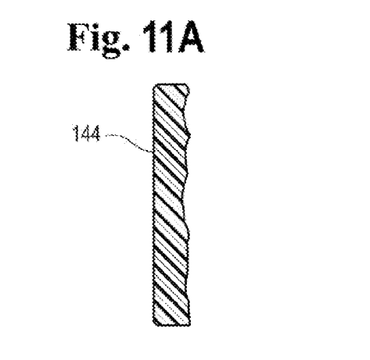
FIG. 11A is a sectional view taken along line 11A-11A of FIG. 11.
Figure 12:
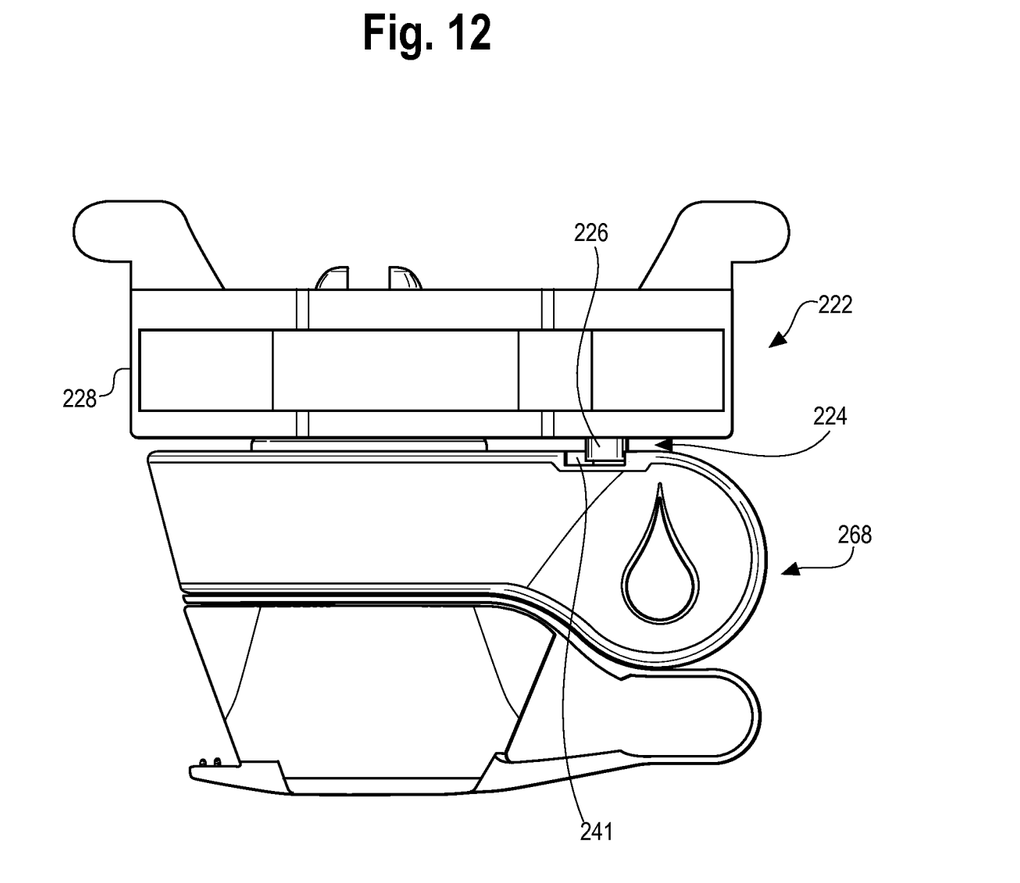
FIG. 12 is a front view of an alternative embodiment of the valve shown, the valve being shown in the closed position.

The valve body 28 is of a known design and, as seen in FIG. 1, has a generally elongated honeycomb shape having diverging/converging ends 32 and an elongated central portion 34. Referring to FIGS. 10-10B, a cylindrical wall 36 defines a stem receiver or receiving region, which wall 36 is partially open as indicated at 38, and as described below. The wall 36 extends through the central portion 34 of the body 28. The illustrated body 28 has angular intersections, indicated generally at 40 in FIG. 1, of the various sides (e.g., central portion 34 with diverging/converging ends 32); however, it will be appreciated by those skilled in the art that the intersections can be rounded as well, and that such configurations are within the scope and spirit of the present disclosure.

The sides of the valve 22, as indicated at 42, can be formed having multiple sealing surfaces or ribs 44, as seen in FIG. 1, or as seen in FIG. 10, can define contiguous planar sealing surfaces 144. The sealing surfaces 44, 144 (whether contiguous or multiple) are configured to provide a region at which the pouch walls 14a,b are sealed to the valve body 28 to effect a seal of the pouch 10 at the lower or bottom end 18.

The valve body 28 includes a well 46, between the side walls 42 and further defined by a bottom wall 48 and the partially open cylindrical wall or stem receiver 36. In a present valve 22, the cylindrical wall 36 serves as a seat such that fluid can pass through the valve body 28 and into the stem portion 30; that is fluid can pass from the well 46 through the opening 38.

The stem portion 30 is positioned for rotation in the stem receiver 36. The stem portion 30 is a hollow tubular member that includes a central bore 50 and an opening 52 in a part of the side wall 54 that, when the valve 22 is in the open position, is aligned with the stem receiver opening 38. In this manner a flow path is provided, as indicated at 56 in FIG. 10B, from the pouch 10, into the valve body well 46, through the aligned openings 38, 52 and out through the stem bore 50. Conversely, when the stem receiver opening 38 and stem opening 52 are not aligned (as seen in FIG. 10A), that is, when the stem portion 30 is rotated 180°, the valve is in the closed position and flow through the valve 22 is stopped. It will be appreciated that the openings 38, 52 are aligned over a portion of the rotation of the stem portion 30, and not just when the stem portion is rotated 180°. Accordingly, rotation of the stem portion 30 can be used to regulate or control flow through the valve at rotations up to and including 180°.

An upper end 58 of the stem portion 30 includes an enlarged head portion or knob 60 that fits into an opening 62 in an upper portion 64 of the valve body 28 to secure the stem portion 30 in place in the valve body 28. The head 60 can be formed with a split configuration, as indicated at 66, to allow a snap-fit of the stem head 60 in the body upper opening 62.

The stem portion 30 includes a grasping region 68 to permit manually rotating the stem portion 30 between the open and closed positions. The grasping region 68 is formed as a two-part member, the first part 70 being a frame or carrier that defines an outer bound 72 of the grasping region 68 and is formed integral with the stem cylindrical wall or tubular portion 36. The second part 74 is a tactile element that is disposed within the frame 70. The tactile element 74 has a different "feel" from the frame portion 70. In a present valve 22, the tactile portion 74 is formed from a material that is softer (e.g., a material having a lower durometer or surface hardness as compared to the material making up the first part 70) and has a higher frictional coefficient than the frame portion 70. It will be appreciated that this higher frictional coefficient provides a no-slip or lesser slip surface than the frame portion 70 for a more positive hold on the stem grasping region 68.

The grasping region 68 also has an enlarged end portion 76. The enlarged end 76 provides a larger area by which a user can grasp and manually manipulate (e.g., rotate) the stem portion 30 to open and close the valve 22. The valve further includes a stop to prevent over-rotation of the valve 30. In a present valve, the stop is formed by a depending stub 77 on the valve body 28 moves into a recess 79 in the grasping portion 68. The stub 77 engages the recess 79 to stop rotation of the stem portion 30.

Figure 2:
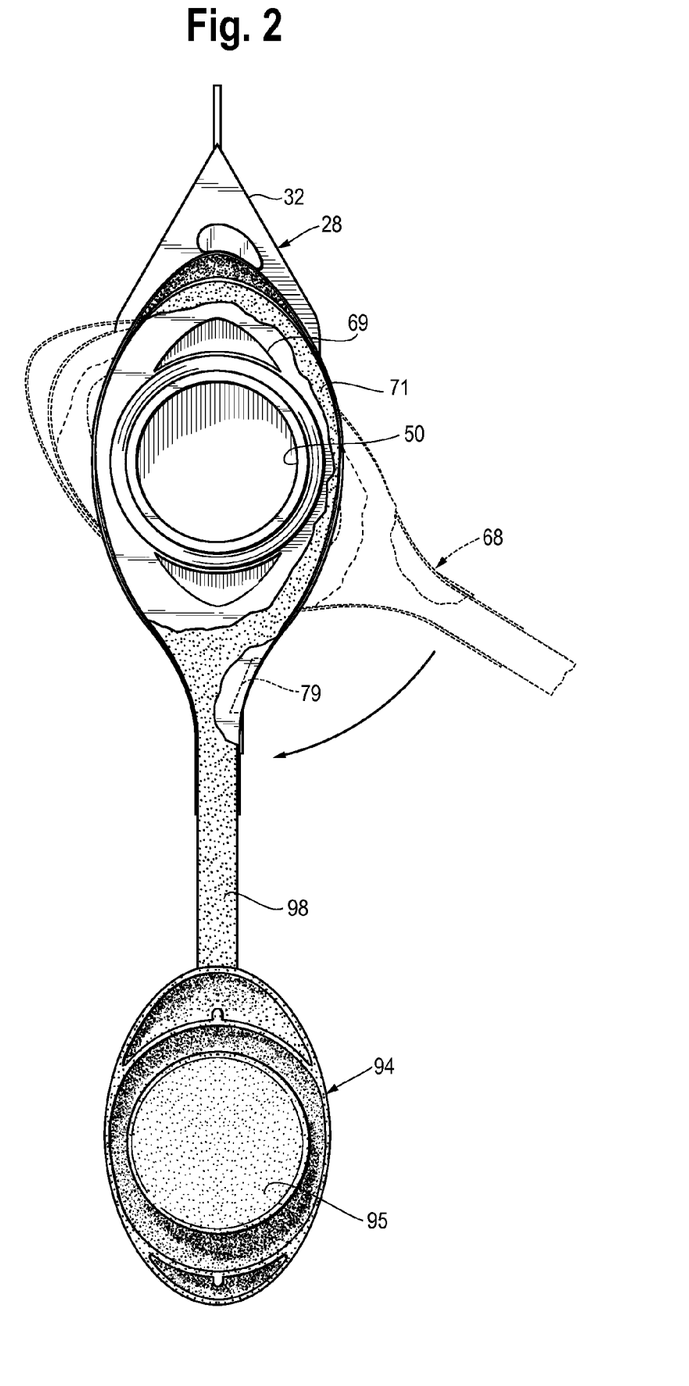
FIG. 2 is a plan view as seen along line 2-2 of FIG. 1.

One side 78 of the end 76 includes an indicator 80 that is sensed by touch (that is, also tactile), so that a user can determine from touch only, the state or position of the valve 22. In a present valve 22, the indicator 80 is a raised element 82 in the shape of a drop or tear-drop that is formed on one side 78 of the end 76; the other side 84 of the end 76 is devoid of the tactile indicator 80 (the raised drop formation 82). The drop formation 82 may be formed as part of and from the same material as the frame 70. In this manner, the drop 82 has a raised surface, raised above the tactile portion 74, and is of a different material than the surrounding tactile portion 74 or frictional surface to provide positive tactile indication of the valve 22 position. Referring briefly to FIG. 2, the grasping region 68, which is an open molded part, includes drainage openings 69 in a bottom surface 71 to permit the drainage of fluid, such therefrom, for example, following a shower during which water may enter the grasping portion 68.

In a present valve 22, the stem portion 30 is molded from a relatively rigid material that when molded and cured or hardened has a relatively smooth finish. One such material is a plastic or polymeric material such as a high density polyethylene (HDPE). The material can include a slip agent formulated with the HDPE to provide smooth manipulation or rotation of the stem portion 30 within the body 28; that is smooth, unfettered movement of the stem portion 30 between the open and closed position.

In a present valve 22, the stem portion 30 is molded as a unitary member, that is molded with the grasping portion frame 70 formed integral with the hollow tubular portion 36. In this configuration, the grasping portion 68 is molded as part of the frame 70, with a bounding wall or edge 72 and a recessed area 86 within the bounding wall 72, and the raised drop formation 82, is also formed as part of and supported by the frame 70.

The higher friction tactile element 74 is positioned within the recessed area 86 in the grasping region 68. In a present valve 22, the higher friction tactile element 74 is molded into the recessed area 86, such as in an overmold process, between the bounding walls 72 and around the raised element 82.

In a present valve 22, the higher friction tactile element 74 may be formed from a thermoplastic elastomer (TPE) such as that available from PolyOne Corp. under the trade name DYNAFLEX®. A current material includes TPE that has a polypropylene resin added at a weigh percent of about 10 percent to the material composition.

Figure 6:
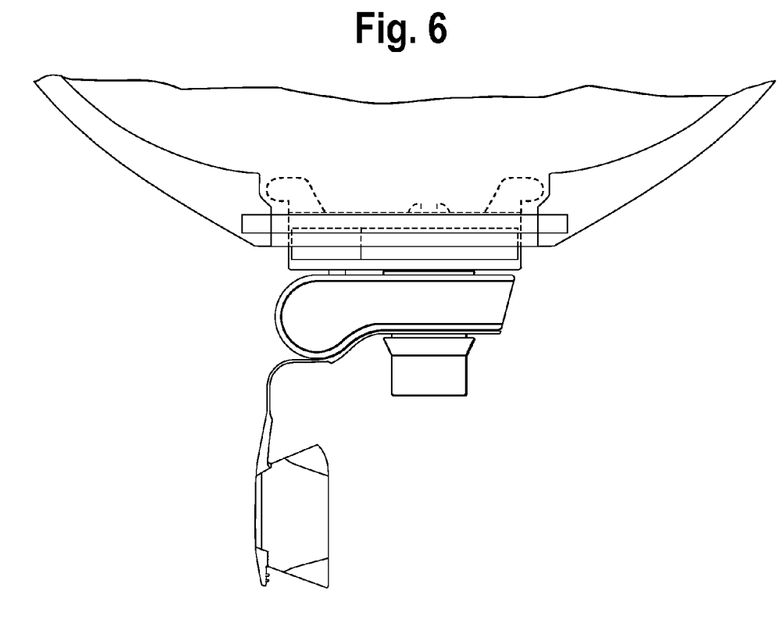
FIG. 6 is a view of the pouch and valve of FIG. 5 shown with the cap removed.

Referring to FIG. 6, the stem portion 30, below the grasping region 68 includes a barb element 88 on the tubular portion 36. The barb element 88 is adapted to permit connecting a discharge tube or other fluid conduit 90 onto the end 92 of the stem portion 30 and to temporarily secure the tube 90 to the stem portion 30.

The valve 22 further includes a cap or closure 94 that is configured to close off the stem end 92. The cap 94 can be formed from a material similar to the grasping region insert 74 (the TPE material) which is sufficiently soft and pliable to allow a user to readily and comfortably position the cap 94 on the stem end 92. The cap 94 can include an inner plug 95 that fits into stem end 92 or rests abutting the end 92 to provide a more secure seal of the valve 22. A present cap 94 includes a ring member 96 that fits over the tubular stem end 92 with a tether 98 to secure the cap 94 to the valve 22. The ring member 96 is configured to be positioned between the barb element 88 and the grasping region 68 to prevent interfering with attachment of the discharge tube 90 to the stem portion 30.

It will be appreciated that when the pouch 10 is worn during the day, the valve 22 will like be closed, and the pouch 10 emptied when it is convenient to the user. When a user is bedridden or during the nighttime, for example when sleeping, the user will likely connect the discharge tube or conduit 90 to the valve 22, leaving the valve 22 open, so that fluids can drain directly to a collection container, such as, for example, a night drainage bag (not shown).

Figure 7:
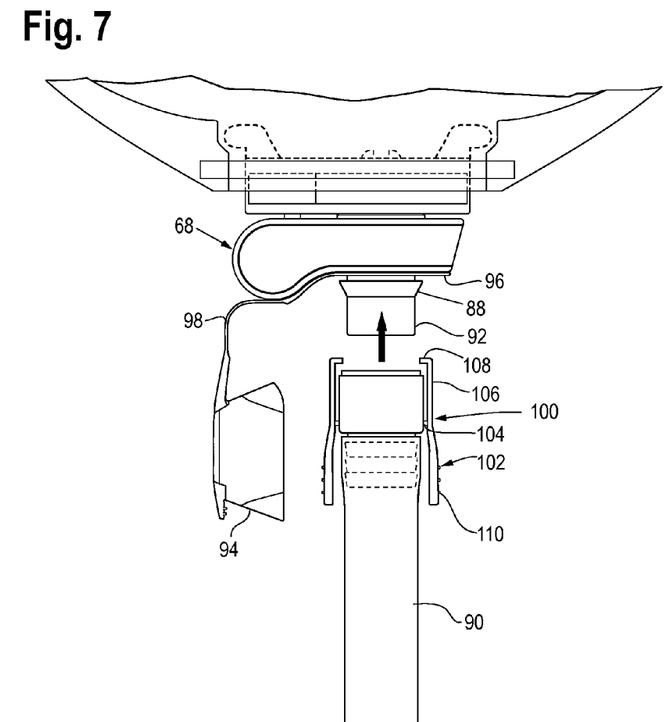
FIG. 7 is a view of the pouch and valve of FIG. 6 with a discharge tube being connected to a stem portion of the valve.
Figure 8:
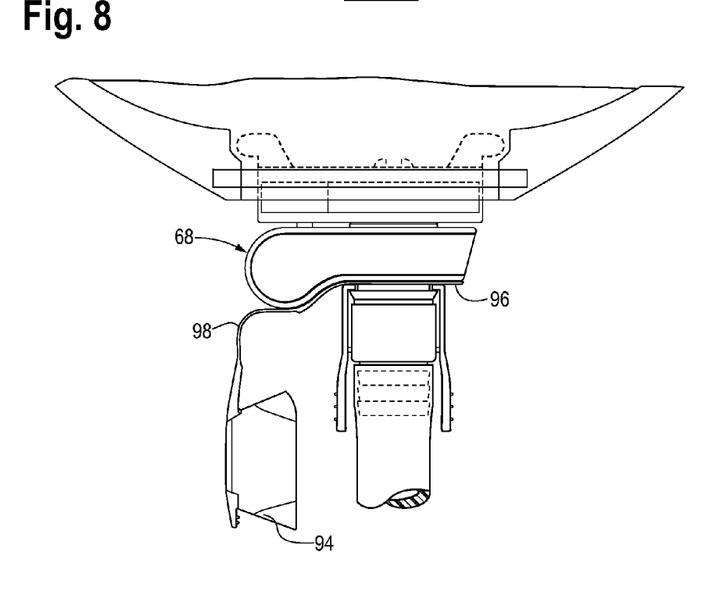
FIG. 8 is a view of the pouch and valve of FIGS. 6 and 7 with the discharge tube connected to the valve stem.
Figure 9:
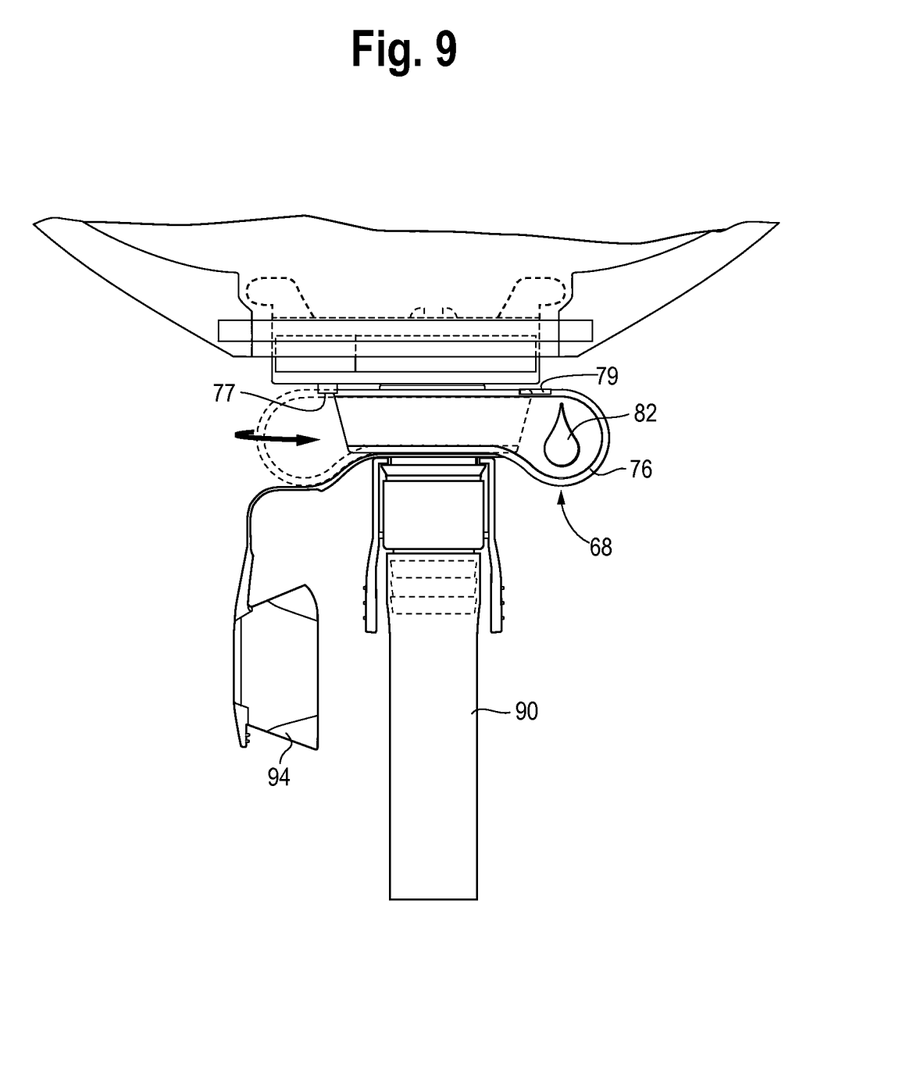
FIG. 9 is a view similar to FIG. 8 with the valve rotated to the open position.

To this end, as seen in FIGS. 7-9, the extension or discharge tube 90 can be attached to the valve stem end 92. The discharge tube 90 includes a connector portion 100 that fits over the stem end 92, and preferably secured to the barb element 88 below the grasping portion 68. It will be understood that the discharge connector portion 100 can be fitted on the stem end 92 when the cap 94 is removed.

The connector portion 100 includes flexible arms 102 that each have a living hinge 104. One end 106 of each arm 102 terminates in an inwardly oriented finger 108. An opposing end 110 of the arm 102 is configured for a user to pinch the arm 102 so as to pivot the arm 102 about the hinge 104. In a resting state, the arms 102 are biased inwardly, toward the tube 90. Thus, when pinching the arms 102 toward one another (inward, toward the tube 90), the fingers 108 are urged Outwardly. The fingers 108 are positioned such that when the discharge tube 90 is connected to the stem end 92, the fingers 108 are located above the barb element 88 as illustrated in FIG. 8. This prevents undesired pull-out of the discharge tube 90 from the stem portion 30.

In a present discharge tube 90, the connector portion 100 is configured such that the connector portion 100 and discharge tube 90 can freely rotate about the stem end 92, without twisting the valve 22. That is, there is sufficient tolerance between the connector portion 100, in conjunction with the stem portion 30 material, to allow the discharge tube 90 to rotate. In this manner, there less opportunity for the tube 90 or pouch 10 to become twisted or pinched if, for example, the user rolls over while resting, which could otherwise reduce or stop flow from the pouch 10. The connection is, however, liquid-tight, to prevent leakage.

It will be appreciated by those skilled in the art that there are many benefits and advantages of the present valve 22. For example, the valve 22 provides both tactile and visual indication of the valve 22 position. In low to no-light conditions, of for users that may have difficultly seeing the valve 22, tactile indication of the valve position will be just one readily and greatly appreciated advantage. Moreover, the softer overmold portion 74 provides a user with a secure grip on the valve grasping region 68 to facilitate readily opening or closing the valve 22. In addition, the valve 22 design, including the tethered cap 94, has an overall pleasing aesthetic, which may be appreciated by some users.

Moreover, the discharge tube connector portion 100, which provides for free rotation about the valve stem end 92, will be understood to reduce the opportunity to twist or pinch the pouch 10 or discharge tube 90, thus providing a higher level of confidence of continued flow when the valve 22 is maintained in the open position.

In an alternate configuration of the valve 222, as seen in FIGS. 12-17A, a detent 224 provides positive positioning of the valve 22 in the full open and full closed positions. In this embodiment, a projection 226 extends downwardly from the valve body 228 that cooperates with a projection 229 on the grasping portion 268 to indicate the fully closed position (FIG. 12) and cooperates with an end 231 of the grasping portion 268 to indicate the fully open (FIG. 13) position.

Figure 15:
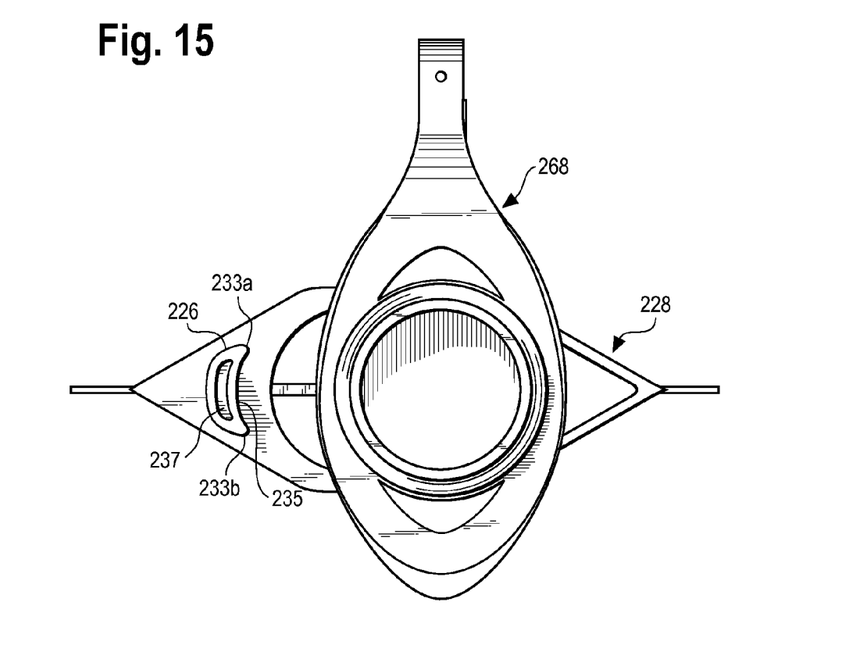
FIG. 15 is a bottom view of the valve in the position of FIG. 14.
Figures 16, 16A:
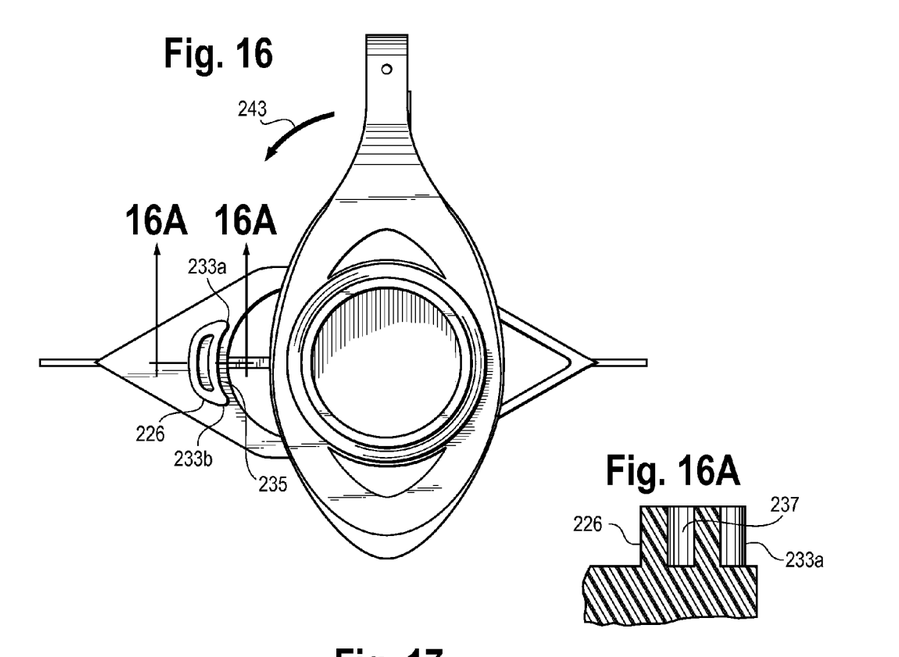
FIG. 16 is a bottom view of the valve, similar to that of FIG. 15 and showing the rotation of the valve grasping portion toward the closed position.
FIG. 16A is a sectional view taken along line 16A-16A of FIG. 16.
Figure 17:
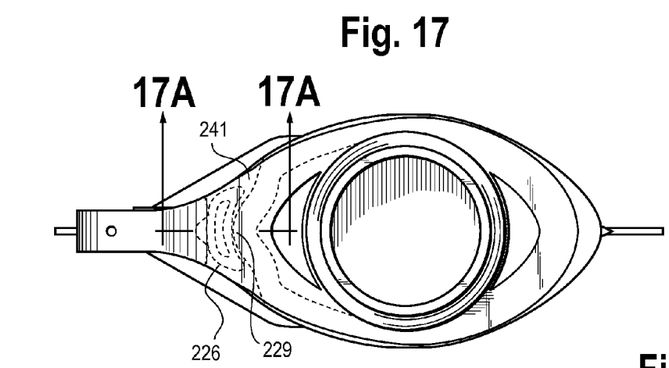
FIG. 17 is a bottom view of the valve similar to that of FIG. 16, showing the cooperation of the detent components in shadowed lines.
Figure 17A:
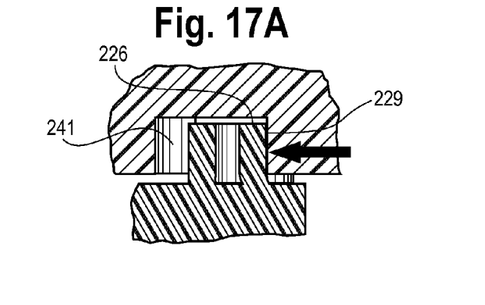
FIG. 17A is a sectional view taken along line 17A-17A of FIG. 17.

Referring to FIGS. 15-16A, the depending body projection 226 can be formed as part of the valve body 228. The projection 226 has an arcuate or inwardly curved shape or concavity, that define contact edges 233a,b and a central receiving region 235, in the direction of the valve stem 230. The projection 226 is formed as a hollow element that permits readily and easily moving the mating portions (e.g., the grasping portion projection 229 and end 231) into and out of contact with the body projection 226. The hollow interior (as indicated at 237) provides a soft and resilient abutment with which the grasping portion 268 cooperates.

As described above, the grasping portion projection is formed on an upper rim 239 that is defined in part by a slot 241 in the rim 239. The projection grasping portion 229 has a complementary arcuate or outwardly curved shape or convexity, that mates and cooperates with the concavity in the body projection 226. As the grasping portion 268 is rotated toward the closed position (as indicated by the arrow at 243 in FIG. 16), the grasping portion projection 229 moves into contact with the body projection 226 and encounters a slight resistance as it contacts one of the respective edges 233a,b. Continued rotation of the grasping portion 268 overcomes the slight resistance and moves the grasping portion projection 229 beyond the edge 233a or b, into the concavity or receiving region 235 on the body projection 226. Fully mating the two projections 229 and 226 provides tactile indication that the valve 222 is in the fully closed position, as there is a slight resistance to move the grasping portion 268 beyond the fully closed position.

Figure 13:
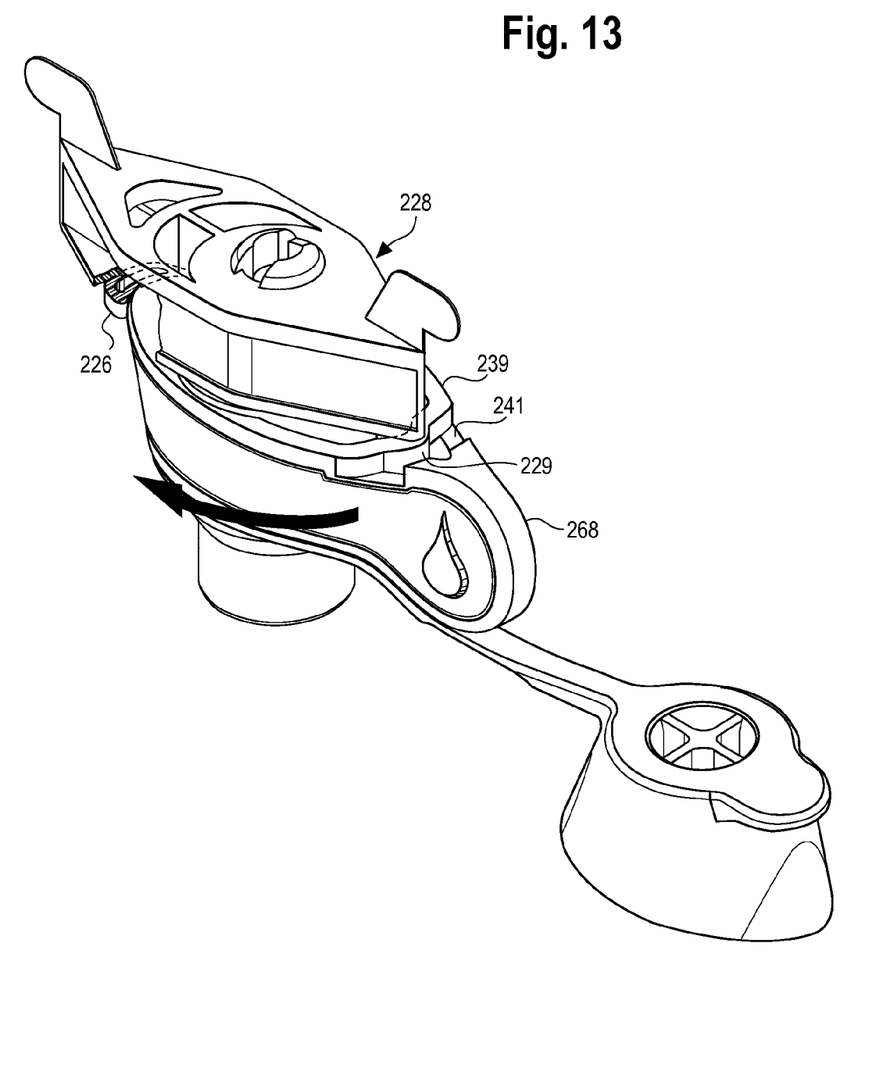
FIG. 13 is a top perspective view of the valve of FIG. 12.
Figure 14:
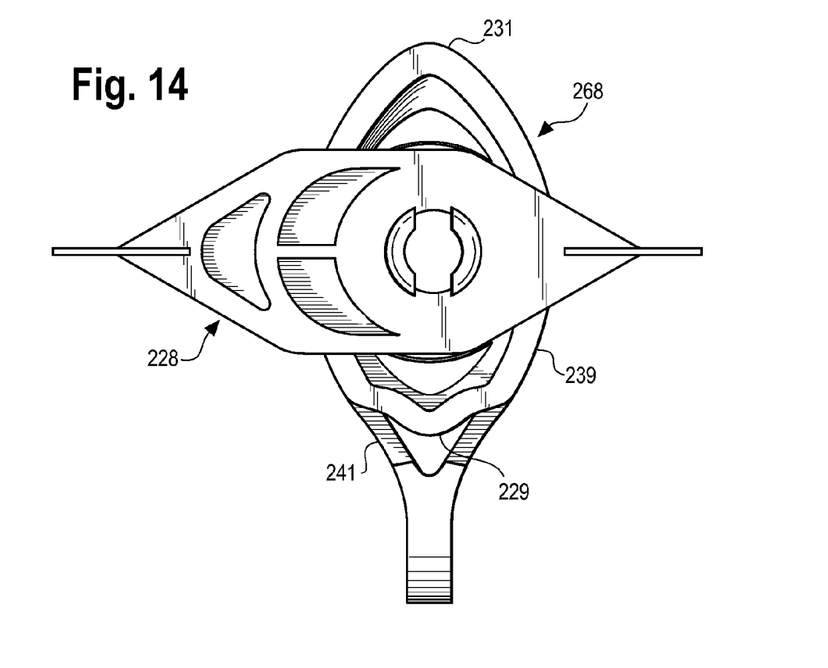
FIG. 14 is a top view of the valve of FIG. 12 shown intermediate the open and closed positions.

From the fully closed position, continued rotation of the grasping portion 268 (which unmates the projections 229 and 226) moves the valve 222 into an intermediate position in which the valve 222 is partially open. Further rotation moves the valve 222 toward the fully open position as illustrated in FIG. 13. In this position, the grasping portion end 231 contacts and cooperates with the valve body projection 226 in much the same manner as grasping portion projection 229. That is, as the grasping portion 268 is rotated toward the open position (the open position being shown in FIG. 13), the grasping portion end 231 moves into contact with the body projection 226 and encounters a slight resistance as it contacts one of the respective edges 233a,b. Continued rotation of the grasping portion 268 overcomes the slight resistance and moves the grasping portion end 231 convexity into the concavity or receiving region 235 on the body projection 226. Fully mating the grasping portion end 231 convexity and the body projection 226 concavity or receiving region 235, provides tactile indication that the valve 222 is in the full open position, as there is a slight resistance to move the grasping portion 268 beyond the fully open position.

All patents referred to herein, are incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A valve that is sealable to an associated container having an interior, the valve adapted to permit and stop flow of fluid from the container interior, the valve comprising:
a valve body sealable to the container, the valve body having a stem receiving region formed therein, the valve body including a fluid receiving region in communication with the container interior;
a stem mounted to the valve body, the stem having a hollow central portion and a sealed upper portion, the stem positioned in the stem receiving region and adapted for rotation within the stem receiving region, the stem including a stem opening in a portion of a wall thereof, the stem being rotatable between an open position to align the stem opening with the valve body fluid receiving region to permit flow from the fluid storage region through the valve, and a closed position to misalign the stem opening with the valve body fluid receiving region to stop flow through the valve,
the stem having a grasping region spaced from the valve body, the grasping region adapted to rotate the stem within the stem receiving region to move the valve between the open and closed positions; and
a detent providing indication of the valve in one or both of the open and closed positions, wherein the detent includes a projection element extending from the valve body configured to operate in conjunction with mating portions formed in the grasping region, wherein the projection element has a curved shape defining contact edges and a central receiving region in the direction of the stem, wherein the mating portions include a first mating portion having a complementary arcuate shape configured to cooperate with the projection element, wherein the first mating portion moves into contact with the projection element as the grasping region is rotated toward the closed position, wherein one of the contact edges provides a resistance as the first mating portion contacts the contact edge, wherein a continuation rotation of the grasping region overcomes the resistance and moves the first mating portion beyond the contact edge into the receiving region in the closed position, wherein the contact edges provide a resistance to move the first mating element beyond the closed position, wherein the detent provides a tactile indication as the first mating portion moves into the receiving region after overcoming the resistance provided by one of the contact edges, wherein the projection element releasably holds the first mating portion in the receiving region in the closed position, wherein the valve stem is configured to rotate 360° such that a further rotation of the grasping region overcomes the resistance provided by the other contact edge and moves the valve to an open position.

2. The valve of claim 1 including a raised portion on a side of the grasping region, wherein the raised portion provides an additional tactile indication, wherein an opposite side of the grasping region being devoid of a raised region.

3. The valve of claim 2 including an insert portion formed on the grasping region, the insert portion being formed from a material that is different from a material of the stem portion.

4. The valve of claim 2 further including an insert portion formed on the grasping region, the insert portion being formed from a material that is different from a material of the stem portion and wherein the raised portion is formed as part of and integral with the stem portion, and wherein the insert portion surrounds, at least in part, the raised portion.

5. A valve that is sealable to an associated container having an interior, the valve adapted to permit and stop flow of fluid from the container interior, the valve comprising:
a valve body sealable to the container; and
a stem mounted to the valve body having a portion in flow communication with the container interior, the stem movable relative to the valve body between an open position to permit flow from the container interior through the valve, and a closed position to stop flow through the valve, the stem having a grasping region spaced from the valve body, the grasping region adapted to rotate the stem to move the valve between the open and closed positions, wherein the grasping region includes an enlarged end portion having first and second side surfaces formed on opposing sides of the enlarged end portion, one of the side surfaces having a tactile indicator to provide indication of the position of the valve, the other of the sides being devoid of the tactile indicator , wherein the tactile indicator is defined by a raised portion on one of the side surfaces, and the other side surface is devoid of the raised portion, wherein the raised portion provides a tactile indication of the valve position by touch and visual distinctions.

6. The valve of claim 5 including an insert portion formed on both the first and second side surfaces of the grasping portion, the insert portion formed from a material that is different from a material of the stem.

7. The valve of claim 6 wherein the grasping portion is formed as a frame in which the insert portion is disposed and wherein the raised portion is formed integral with the frame.

8. The valve of claim 6 wherein the insert portion is formed from a relatively soft material having a higher frictional coefficient than the stem material.

9. The valve of claim 8 wherein the insert portion is formed from a thermoplastic elastomer.

10. The valve of claim 5 and including a cap, the cap being removable from a discharge end of the valve.

11. The valve of claim 10 wherein the cap is tethered to the valve.

12. The valve of claim 10 wherein the cap is formed from the insert portion material.

13. The valve of claim 5 including a detent to provide indication of the valve in one or both of the open and closed positions.

14. An ostomy pouch, comprising:
a pouch having first and second walls sealed to one another at about their respective peripheries defining an interior fluid storage region, an inlet and an outlet; and
a valve sealed to the first and second walls at about the outlet, the valve adapted to permit and stop flow of fluid from the fluid storage region, the valve having a valve body and a stem mounted to the valve body having a portion in flow communication with the fluid storage region, the stem movable relative to the valve body between an open position to permit flow from the fluid storage region through the valve, and a closed position to stop flow through the valve, the stem having a grasping region spaced from the valve body, the grasping region adapted to rotate the stem to move the valve between the open and closed positions, wherein the grasping region includes an enlarged end portion having first and second side surfaces formed on opposing sides of the enlarged end portion, one of the side surfaces having a tactile indicator to provide indication of the position of the valve, the other of the sides being devoid of the tactile indicator wherein the tactile indicator is defined by a raised portion on one of the side surfaces, and the other side surface is devoid of the raised portion, wherein the raised portion provides a tactile indication of the valve position by touch and visual distinctions.

15. The ostomy pouch of claim 14 including an insert portion formed on both the first and second side surfaces of the grasping portion, the insert portion formed from a material that is different from a material of the stem.

16. The ostomy pouch of claim 15 wherein the grasping portion is formed as a frame in which the insert portion is disposed and wherein the raised portion is formed integral with the frame.

17. The ostomy pouch of claim 16 wherein the insert portion is formed from a relatively soft material having a higher frictional coefficient than the stem material.

18. The ostomy pouch of claim 17 wherein the insert portion is formed from a thermoplastic elastomer.

19. The ostomy pouch of claim 14 wherein the valve includes a detent to provide indication of the valve in one or both of the open and closed positions.

20. The valve of claim 5, wherein the valve is mounted to an ostomy pouch and configured for draining the ostomy pouch.

* * * * *